United States Patent [19]

Klar

[11] Patent Number: 5,853,706
[45] Date of Patent: Dec. 29, 1998

[54] SCENTED HAIR GEL HAVING PARTICULATE MATTER IN THE FORM OF GLITTER

[75] Inventor: Cindi Klar, New York, N.Y.

[73] Assignee: Townley Jewelry, Inc., New York, N.Y.

[21] Appl. No.: 820,759

[22] Filed: Mar. 19, 1997

[51] Int. Cl.$^6$ ...................................................... A61K 7/06
[52] U.S. Cl. ...................... 424/70.1; 424/70.2; 424/70.6; 424/70.11; 424/70.13; 424/70.15; 424/74
[58] Field of Search .................... 424/70.1, 70.2, 424/70.6, 70.11, 70.13, 70.15, 74, 795.1

[56] References Cited

U.S. PATENT DOCUMENTS

| | | | |
|---|---|---|---|
| 4,915,935 | 4/1990 | Corbett et al. | 424/47 |
| 5,518,736 | 5/1996 | Magdassi et al. | 424/451 |
| 5,641,480 | 6/1997 | Vermeer | 424/70.24 |

*Primary Examiner*—Neil S. Levy
*Attorney, Agent, or Firm*—Ezra Sutton

[57] ABSTRACT

A hair gel composition having glitter contained therein comprising a surface active hair treatment system for moisturizing, conditioning, and lubricating the hair and scalp, and for holding stylized hair in place, in the range of 7.5% to 10.0% by weight of the hair gel composition; at least one pH adjuster being in the range of 0.5% to 2.0% by weight of the hair gel composition; a preservative system for preserving the hair gel composition against microbial contamination being in the range of 0.40% to 2.4% by weight of the hair gel composition; at least one anti-oxidant and light stabilizer for preventing oxidation of the hair gel composition being in the range of 0.02% to 0.3% by weight of the hair gel composition; a diluent in the form of water in the range of 80.0% to 95.0% by weight of the hair gel composition; and suspended particulate matter for aesthetic ornamentation of the hair being in the range of 2.0% to 5.0% by weight of the hair gel composition.

3 Claims, No Drawings

SCENTED HAIR GEL HAVING PARTICULATE MATTER IN THE FORM OF GLITTER

FIELD OF THE INVENTION

The invention relates to a novel scented hair gel composition which, when applied to the human hair, provides glitter, moisture conditioning, body, and protection to the hair and scalp. More particularly, this invention relates to a hair gel having aesthetic qualities of fragrance, conditioning, holding a hair style, color, and particulate matter in the form of glitter, and which fulfills the guidelines for hair grooming ingredients established by the Food and Drug Administration, as listed in the Federal Register: Volume 43, Number 166.

BACKGROUND OF THE INVENTION

Hair gels are categorized as either styling and sculpting gels or as activator and conditioning gels. Styling gels are designed to confer hair-holding properties, whereas the conditioning gels primarily facilitate grooming and assist in the prevention of hair damage.

Hair gel compositions are widely used by females and males for hair grooming and conditioning in which the hair gel imparts cosmetic qualities of softer and moisturized hair to the user while keeping the hair in place after styling. Users of hair gels are desirous of improved hair gels for improved hair grooming that will impart aesthetic qualities to heighten a female's or male's appearance, beauty or sex appeal.

There remains a need for a scented hair gel which enhances the hair grooming, and the cosmetic and aesthetic qualities for females or males, wherein the hair gel product would include a moisturizer, a fragrance, a conditioner, a hair set polymer, a color, and a glitter or sparkling effect to the wearer's hair. In addition, the hair gel would have improved holding ability for hair styling and would not be excessively stiff.

DESCRIPTION OF THE PRIOR ART

Hair grooming compositions, hair tonics, hair dressings, hair pomades, hair gels, hair mousses, hair sprays, hair treatment preparations, and the like have been disclosed in the prior art. For example, U.S. Pat. No. 604,111 discloses a hair tonic of mountain sage, glycerin, tincture of lobella, prickly pear juice, tincture of capsicum, seed oil, and alcohol, which cleans the scalp, relaxes and stimulates the scalp, cools the scalp and gives the hair gloss.

U.S. Pat. No. 3,932,611 discloses a composition for hair and scalp care comprising white petroleum jelly, beeswax, coconut oil, olive oil, castor oil, oil of sassafras and oil of cinnamon. The composition allegedly inhibits scaling of dandruff particles.

U.S. Pat. No. 4,002,734 discloses a composition for grooming or dressing hair comprising petroleum, rectified tar oil, phenol, sulfur, oxyquinoline, pine oil and castor oil in a petroleum jelly base. The composition allegedly inhibits scaling of dandruff particles.

U.S. Pat. No. 4,230,689 discloses hydrating a mixture of rice with mung bean by heating at 75°–212°F. with a cup of Ginseng tea, recovering and condensing the vapors and using the condensate for grooming or dressing hair.

U.S. Pat. No. 4,300,580 discloses a hair grooming composition that includes a linear polyester derived from at least one dicarboxylic acid, at least one diol being 20 mole % of polyethylene glycol and a difunctional monomer containing a $^-SO_3M$ group attached to an aromatic nucleus.

U.S. Pat. No. 4,511,555 discloses a composition for grooming or dressing hair comprising an acceptable carrier, and a vegetable oil extract of sage, Indian hemp and rosemary. The composition is used in pomades and shampoos.

U.S. Pat. No. 4,915,935 to Corbett et al discloses a process for applying reflective particles ("glitter") to hair in the form of a styling foam (mousse). The styling foam composition has chemical ingredients that include a foaming agent, water-soluble hair setting resins, a propellant component, suspended particulate matter ("glitter"), and water. The chemicals in the '935 patent are used to form several variations of a styling mousse. This prior art patent does not teach a hair gel having the composition of the present invention.

U.S. Pat. No. 4,950,475 discloses a (hair) gel composition that includes a water dissipatable polymer in the form of an emulsion, humectants, emollients, water, coloring agents and pigments, preservatives, medical agents, cosmetic agents, and agents to modify the refractive index of the gel.

U.S. Pat. No. 5,000,949 discloses a hair grooming composition which promotes scalp and hair health, and hair growth that includes petroleum jelly, an oil extract of cactus, glycerin and oil of clover or other odorant.

U.S. Pat. No. 5,266,303 discloses an aerosol hair spray formulation containing a sulfonate-containing (water-dispersible or water-dissipatible) linear polyester; a water-soluble, polyvinyl lactim polymer; water and a propellant.

U.S. Pat. No. 5,266,308 discloses a hair treatment composition that includes a water-insoluble, dispersible polymeric resin; a water-soluble polymeric resin; a water-soluble polymer; and water. Water-insoluble resins include chemical compounds from the group consisting of a diglycol, a cyclohexanedimethanol, isophthalates, or sulfoisophthalates polyester. The water-soluble polymeric resin is a copolymer of polyvinylpyrrolidone and vinyl acetate. The water-soluble polymer is a polyvinylpyrrolidone.

U.S. Pat. No. 5,441,728 discloses an aqueous hair treatment (hairspray) composition that includes a water-soluble polymer; and a latex of water-insoluble particles dispersed in water. The latex particles are formed from respective monomers by emulsion polymerization.

None of the prior art patents teach or disclose the ingredient composition of the hair gel of the present invention that includes a fragrance, a moisturizer, a colorant and suspended particulate matter in the form of glitter in which the hair gel is hypoallergenic and safe for the user.

Accordingly, it is an object of the present invention to provide a hair gel having an ingredient composition that includes suspended particulate matter in the form of glitter made from a colorized polyester glitter contained therein.

Another object of the present invention is to provide a hair gel having an ingredient composition that also includes a fragrance, a moisturizer, and a colorant.

Another object of the present invention is to provide a hair gel that is made from hair grooming ingredients that are hypoallergenic and safe for the user to apply to the hair and scalp.

Another object of the present invention is to provide a hair gel that imparts hair grooming characteristics and aesthetic qualities which enhance a male's or female's appearance, beauty and sex appeal.

Another object of the present invention is to provide a hair gel that is easy to apply and easy to remove and clean-off when the user deems it necessary to remove the glitter from the user's hair and scalp by using a standard shampoo.

A further object of the present invention is to provide a hair gel that is long-lasting, durable in application and reliable in providing hair grooming and conditioning.

A still further object of the present invention is to provide a hair gel that may be mass produced in an automated and economical manner and is readily affordable by the consumer.

SUMMARY OF THE INVENTION

In the present invention, there is provided a hair gel composition having glitter contained therein, including a surface active hair treatment system for moisturizing, conditioning, and lubricating the hair and scalp, and for holding stylized hair in place, in the range of 7.5% to 10.0% by weight of the hair gel composition; at least one pH adjuster in the range of 0.5% to 2.0% by weight of the hair gel composition; a preservative system for preserving the hair gel composition against microbial contamination in the range of 0.40% to 2.4% by weight of the hair gel composition; at least one anti-oxidant and light stabilizer for preventing oxidation of the hair gel composition in the range of 0.02% to 0.3% by weight of the hair gel composition; a diluent in the form of water in the range of 80% to 95% by weight of the hair gel composition; and suspended particulate matter for aesthetic ornamentation of the hair in the range of 2.0% to 5.0% by weight of the hair gel composition.

The hair gel composition of the present invention may further include a fragrance component for imparting a characteristic scent to the hair gel being in the overall range of 0.05% to 2.0% by weight of the hair gel composition; and a colorant for imparting a characteristic color to the hair gel being in the overall range of 0.10% to 2.0% by weight of the hair gel composition.

DETAILED DESCRIPTION OF THE PREFERRED EMBODIMENTS

In accordance with the hair gel composition of the present invention, the ingredient categories of the constituent components include a surface active hair treatment system, pH adjusters, a preservative system, an anti-oxidant and light stabilizer, water, a fragrance, a colorant, and suspended particulate matter.

The surface active hair treatment system of the hair gel composition of the present invention is functionally defined to include one or more chemical constituents that are chelates, conditioners, emollients, gellants, humectants, lubricants, moisturizers, polymers for hair setting, proteins, solubilizers thickeners, and/or thixotropies. The hair treatment system of the hair gel composition of the present invention is used for providing to the user the ability to retain moisture in the hair and scalp to increase the moisture content of the hair and scalp (skin) through humectant barrier action; to provide conditioning, protein, and emollient agents which when applied to the hair strands on the user's head become soft and manageable; and to provide gellants and polymers for hair setting which when applied to the hair they act to hold the hair in place. The surface active hair treatment system for moisturizing the hair and scalp and for styling and holding the hair in place as previously described above, includes chemical agents selected from the group consisting of propylene glycol, Carbomer 940™, PVP-dimethyaminoethylmethacrylate copolymer, acrylates-steareth-20 methylacrylate copolymer, polyvinylpyrrolidone, polyquaternuim-11, PVP/VA copolymers, disoduim EDTA, EDTA, malic acid, dimethicone copoyol, Poloxamer 235™, oleth-10 phosphate, carrageenan, panthenol, petrolatum, dimethicone, dimethiconecopolyol, bentonite, silk amino acids, decolorized aloe vera gel, honey extract, glycerin, mineral oil, lanolin, hydrolyzed animal protein, collagen amino acids, triethanolamine, thixagel, hectorite, sepigel, trisodium EDTA, sodium aspartate, polysorbate, equivalent chemical agents and combinations thereof. The surface active hair treatment system is at least 7.5% by weight of the hair gel composition and has an overall range of 7.5 to 10.0 by weight of the hair gel composition.

The pH adjusters for the hair gel composition of the present invention are functionally defined to include chemical constituents that are acidulents, alkalinizers, buffers and/or neutralizers. The pH adjusters for the hair gel composition of the present invention are used for neutralizing or buffering the hair gel composition from an acidic or basic condition to a neutral pH of 7. The pH adjusters for neutralizing of the hair gel are selected from the group consisting of sodium hydroxide, citric acid, triethanolamine, diethanolamine, glycine, ethanolamine, tromethamine, equivalents and combinations thereof, being in the overall range of 0.5% to 2.0% by weight of the hair gel composition.

The preservative system for the hair gel composition of the present invention is functionally defined to include chemical constituents that are antibacterial, antimicrobial and preservative agents for protecting the hair gel composition from spoilage or contamination by microorganisms. The preservative system for protecting the user and the hair gel composition against microbial contamination, as described above, are chemical agents selected from the group consisting of imidozolidinyl urea, methylparaben, propylparaben, benzylparaben, isopropylparaben, ethylparaben, Germaben II™, phenoxyisopropanol, Phenonip™, DMDM hydantoin, hexetidine, sorbic acid, honeysuckle extract, Iceland moss extract, equivalents and combinations thereof, being in the overall range of 0.40% to 2.4% by weight of the hair gel composition.

The anti-oxidant and light stabilizer for the hair gel composition of the present invention is defined to include chemical agents that are antioxidants and ultraviolet light absorbers. These chemical stabilizer agents are used to inhibit oxidation, rancidity, and protect the hair gel composition from degradation by ultraviolet light radiation. These anti-oxidant and light stabilizers for protecting the hair gel against oxidation and UV light damage, as described above, are chemical agents selected from the group consisting of benzophenone-2, benzophenone-4, octyl dimethyl PABA, octyl methoxycinnamate, BHA, octyl salicylate, ascorbic acid, isopropyl methoxycinnamate, equivalents and combinations thereof; being in the overall range of 0.02% to 0.3% by weight of the hair gel composition.

The suspended particulate matter used for the hair gel composition of the present invention is defined to include a pearlant chemical gannet that imparts a glitter, a sparkle or a pearlescent texture and luster to the hair gel product when exposed to natural or artificial light. These pearlant compounds are used for aesthetic ornamentation on the hair of the user's head. The suspended particulate matter of the present invention is selected from the group consisting of colorized acrylic polyesters, metallic and non-metallic micas, bismuth oxychloride, organic guanines (fish scales), equivalents and combinations thereof, being in the overall range of 2.0% to 5.0% by weight of the hair gel composition.

The fragrance (perfume) component of the hair gel composition of the present invention is defined to impart a particular scent or characteristic aroma to the hair gel composition. The use of a fragrance or perfume in the hair gel composition provides an enhanced aesthetic quality to the hair gel composition which heightens a male's or a female users' appearance, handsomeness, beauty and sex appeal. The fragrance component is selected from the group consisting of botanical extracts that include balm mint, birch, chamomile, fir, heather, honey suckle, ivy, jasmine, lotus, pine, rose, soapwort, violet, willow bark, winter green, witch hazel, yucca, and equivalents and combinations thereof, being in the overall range of 0.05% to 2.0% by weight of the hair gel composition.

The colorant component for the hair gel composition of the present invention is defined to impart a characteristic color in conjunction with a particular fragrance to the hair gel composition. For example, a yellow color is used for a banana scent, or a pink color for a floral-type scent. The colorant component is selected from the group consisting of water soluble dyes that include FD&C dyes (food, drug, and cosmetic use dyes) or D&C dyes (drug and cosmetic) of blue, green, orange, red, yellow and violet; iron oxide dyes; ultramarine pigments of blue, pink, red and violet; and equivalents thereof; being in the overall range of 0.10% to 2.0% by weight of the hair gel composition. Specific examples of FD&C or D&C colorants that may be used are blue #1, green #3, green #8, red #4, red #33, red #40, violet #2, yellow #5, and yellow #10. The dyes discussed above are well known, and are commercially available materials, with their chemical structure being described, e.g., in 21 C.F.R. Part 74 (as revised Apr. 1, 1988) and the CTFA Cosmetic Ingredient Handbook, (1988), published by the Cosmetics, Toiletry and Fragrancy Association, Inc.

The diluent or carrier is in the form of water in the overall range of 80.0% to 95.0% by weight of the hair gel composition.

The following numbered examples illustrate representative hair gel formulations embodying the present invention in using a scent or fragrance, a moisturizer, a conditioner, a colorant and suspended particulate matter within the hair gel composition.

EXAMPLE 1

Product Description: Unscented Clear Glitter Hair Gel

| CHEMICAL COMPONENT | PERCENTAGE BY WEIGHT |
| --- | --- |
| Water | 80.00–95.00 |
| Polyester glitter | 2.00–5.00 |
| Propylene glycol | 1.00–2.00 |
| Carbomer 940 | 0.50–2.00 |
| Polyvinylpyrrolidone | 0.50–2.00 |
| Triethanolamine | 0.50–2.00 |
| Imidozolidinyl urea | 0.20–1.00 |
| Methylparaben | 0.20–1.00 |
| Disodium EDTA | 0.10–0.75 |
| Propylparaben | 0.02–0.40 |
| Benzophenone-4 | 0.02–0.30 |

EXAMPLE 2

Product Description: Unscented Clear Glitter Hair Gel

| CHEMICAL COMPONENT | PERCENTAGE BY WEIGHT |
| --- | --- |
| Water | 80.00–95.00 |
| Polyester glitter | 2.00–5.00 |
| Acrylates-steareth-20 methylacrylate copolymer | 2.00–4.00 |
| Propylene glycol | 1.00–2.00 |
| Polyvinylpyrrolidone | 0.50–2.00 |
| Triethanolainine | 0.50–2.00 |
| Imidozolidinyl urea | 0.20–1.00 |
| Methylparaben | 0.20–1.00 |
| Disodium EDTA | 0.10–0.75 |
| Propylparaben | 0.02–0.40 |
| Benzophenone-4 | 0.02–0.30 |

EXAMPLE 3

Product Description: Unscented Clear Glitter Hair Gel

| CHEMICAL COMPONENT | PERCENTAGE BY WEIGHT |
| --- | --- |
| Water | 80.00–95.00 |
| Polyester glitter | 2.00–5.00 |
| PVP-Dimethylamino-ethylmethacrylate Copolymer | 2.00–4.00 |
| Propylene glycol | 1.00–2.00 |
| Polyvinylpyrrolidione | 0.50–2.00 |
| Tiethanolamine | 0.50–2.00 |
| Imidozolidinyl urea | 0.20–1.00 |
| Methylparaben | 0.20–1.00 |
| Disodium EDTA | 0.10–0.75 |
| Propylparaben | 0.02–0.40 |
| Benzophenone-4 | 0.02–0.30 |

EXAMPLE 4

Product Description: Scented Glitter Hair Gel for Women

| CHEMICAL COMPONENT | PERCENTAGE BY WEIGHT |
| --- | --- |
| Water | 80.00–95.00 |
| Polyester glitter | 2.00–5.00 |
| Acrylates-steareth-20 MA copolymer | 2.00–4.00 |
| Propylene glycol | 1.00–2.00 |
| Polyvinylpyrrolidone | 0.50–2.00 |
| Triethanolamine | 0.50–2.00 |
| Imidozolidinyl urea | 0.20–1.00 |
| Methylparaben | 0.20–1.00 |
| Disodium EDTA | 0.10–0.75 |
| Propylparaben | 0.02–0.40 |
| Benzophenone-4 | 0.02–0.30 |
| Floral fragrance | 0.20–3.0 |

EXAMPLE 5

Product Description: Scented and Colored Glitter Hair Gel

| CHEMICAL COMPONENT | PERCENTAGE BY WEIGHT |
|---|---|
| Water | 80.00%–95.00% |
| Polyester glitter | 2.00–5.00 |
| PVP-dimethylamino-ethylinethacrylate Copolymer | 2.00–4.00 |
| Propylene glycol | 1.00–2.00 |
| PVP | 0.50–2.00 |
| Carbomer 940 | 0.50–2.00 |
| Triethanolamine | 0.50–2.00 |
| Imidozolidinyl urea | 0.20–1.00 |
| Methylparaben | 0.20–1.00 |
| Disodium EDTA | 0.10–0.75 |
| Propylparaben | 0.02–0.40 |
| Benzophenone-2 | 0.02–0.30 |
| Fir fragrance | 0.20–3.00 |

EXAMPLE 6

Product Description: Scented and Colored Glitter Hair Gel for Women

| CHEMICAL COMPONENT | PERCENTAGE BY WEIGHT |
|---|---|
| Water | 80.00–95.00 |
| Polyester glitter | 2.00–5.00 |
| PVP-Dmaema Copolymer | 2.00–4.00 |
| Propylene glycol | 1.00–2.00 |
| PVP | 0.50–2.00 |
| Carbomer 940 | 0.50–2.00 |
| Triethanolamine | 0.50–2.00 |
| Imidozolidinyl urea | 0.20–1.00 |
| Methylparaben | 0.20–1.00 |
| Disodium EDTA | 0.10–0.75 |
| Propylparaben | 0.02–0.40 |
| Benzophenone-2 | 0.02–0.30 |
| Rose fragrance | 0.20–3.00 |
| Ultramarine pink pigment | 0.10–2.00 |

EXAMPLE 7

Product Description: Scented and Colored Glitter Hair Gel for Men

| CHEMICAL COMPONENT | PERCENTAGE BY WEIGHT |
|---|---|
| Water | 80.00–95.00 |
| Polyester glitter | 2.00–5.00 |
| PVP-VA Copolymer | 2.00–4.00 |
| Propylene glycol | 1.00–2.00 |
| PVP | 0.50–2.00 |
| Carbomer 940 | 0.50–2.00 |
| Triethanolamine | 0.50–2.00 |
| Imidozolidinyl urea | 0.20–1.00 |
| Methylparaben | 0.20–1.00 |
| Disodium EDTA | 0.10–0.75 |
| Propylparaben | 0.02–0.40 |
| Benzophenone-2 | 0.02–0.30 |
| Winter green fragrance | 0.20–3.00 |
| D & C Green #8 | 0.10–2.00 |

EXAMPLE 8

Product Description: Organic Glitter Hair Gel for Women

| CHEMICAL COMPONENT | PERCENTAGE (%) BY WEIGHT |
|---|---|
| Water | 80.00–95.00 |
| Guanine | 2.00–5.00 |
| Aloe vera gel | 1.00–2.00 |
| Thixagel | 0.50–2.00 |
| Citric acid triethanolamine | 0.50–2.00 |
| Imidozolidinyl urea | 0.20–1.00 |
| DMDD hydantoin | 0.20–1.00 |
| Polysorbate | 0.10–0.75 |
| Honeysuckle extract | 0.02–0.40 |
| Ascorbic acid | 0.02–0.30 |
| FD & C yellow dye #5 | 0.10–2.00 |
| Banana fragrance | 0.20–4.00 |

ADVANTAGES OF THE PRESENT INVENTION

Accordingly, an advantage of the present invention is that it provides for a hair gel having an ingredient composition that includes suspended particulate matter in the form of glitter made from a colorized polyester glitter contained therein.

Another advantage of the present invention is that it provides for a hair gel having an ingredient composition that also includes a fragrance, a moisturizer, and a colorant.

Another advantage of the present invention is that it provides for a hair gel that is made from hair grooming ingredients that are hypoallergenic and safe for the user to apply to the hair and scalp.

Another advantage of the present invention is that it provides for a hair gel that imparts hair grooming characteristics and aesthetic qualities which enhance a male's or a female's appearance, beauty and sex appeal.

Another advantage of the present invention is that it provides for a hair gel that is easy to apply and easy to remove and clean-off when the user deems it necessary to remove the glitter from the user's hair and scalp by using a standard shampoo.

A further advantage of the present invention is that it provides for a hair gel that is long-lasting, durable in application and reliable in providing hair grooming and conditioning.

A still further advantage of the present invention is that it provides for a hair gel that may be mass produced in an automated and economical manner and is readily affordable by the consumer.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A hair gel composition having glitter contained therein, comprising:

a) a surface active hair treatment system for moisturizing, conditioning, and lubricating the hair and scalp, and for holding stylized hair in place, selected from the group consisting of propylene glycol, polyvinylpyrrolidone-dimethyaminoethylmethacrylate copolymer, acrylates-steareth-20, methylacrylate copolymer, polyvinylpyrrolidone, polyvinylpyrrolidone vinyl acetate (PVP/VA) copolymers disodium ethylenediaminetetraacetate (EDTA), EDTA, malic acid, panthenol, petrolatum, aloe vera gel, glycerin, mineral oil, lanolin, collagen amino acids, bentonite, triethanolamine, thixagel, hectorite, sepigel, sodium aspartate, polysorbate and combinations thereof; being in the range of 7.5% to 10.0% by weight of the hair gel composition;

b) at least one pH adjuster selected from the group consisting of triethanolamine, diethanolamine, glycine, ethanolamine, tromethamine, and combinations thereof; being in the range of 0.5% to 2.0% by weight of the hair gel composition;

c) a preservative system for preserving the hair gel composition against microbial contamination selected from the group consisting of urea, sorbic acid, hexetidine, honeysuckle extract, Iceland moss extract and combinations thereof; being in the range of 0.40% to 2.4% by weight of the hair gel composition;

d) at least one anti-oxidant and light stabilizer for preventing oxidation of the hair gel composition selected from the group consisting of benzophenone-2, benzophenone-4, octyl dimethyl para-aminobenzoic acid (PABA), octyl methoxycinnamate, octyl salicylate, ascorbic acid, isopropyl methoxycinnamate and combinations thereof, being in the range of 0.02% to 0.3% by weight of the hair gel composition;

e) a diluent in the form of water in the range of 80.0% to 95.0% of the hair gel composition; and f) suspended particulate matter for aesthetic ornamentation of the hair being colorized acrylic polyester and micas and being in the range of 2.0% to 5.0% by weight of the hair gel composition.

2. A hair gel composition in accordance with claim 1, further including a fragrance component for imparting a characteristic scent to said hair gel composition selected from the group consisting of botanical extracts that include balm mint, birch, chamomile, fir, heather, honey suckle, ivy, jasmine, lotus, pine, rose, soapwort, violet willow bark, winter green, witch hazel, yucca; being in the overall range of 0.05% to 2.0% by weight of the hair gel composition.

3. A hair gel composition in accordance with claim 1, further including a colorant component for imparting a characteristic color to said hair gel composition selected from the group consisting of water soluble dyes of blue, green, orange, red, violet, and yellow; iron oxide dyes; ultramarine pigments of blue, pink, red, and violet; and FD&C colorants of blue #1, green #3, green #8, red #4, red #33, red #40, violet #2, yellow #5, yellow #10; being in the overall range of 0.10% to 2.0% by weight of the hair gel composition.

* * * * *